United States Patent [19]
Roumagnac et al.

[11] Patent Number: 5,381,726
[45] Date of Patent: Jan. 17, 1995

[54] HOLDER FOR OBJECTS INSIDE A ROTATING DRUM

[75] Inventors: Jean-Patrick Roumagnac, Le Coteau; Francisco Naveros, Roanne, both of France

[73] Assignee: Barriquand Steriflow, Roanne, France

[21] Appl. No.: 50,287

[22] PCT Filed: Oct. 28, 1991

[86] PCT No.: PCT/FR91/00848
§ 371 Date: May 7, 1993
§ 102(e) Date: May 7, 1993

[87] PCT Pub. No.: WO92/08498
PCT Pub. Date: May 29, 1992

[30] Foreign Application Priority Data
Nov. 8, 1990 [FR] France .................. 90 13883

[51] Int. Cl.6 ............................ A23L 3/10
[52] U.S. Cl. ...................... 99/371; 99/483; 100/287
[58] Field of Search ............. 99/369, 371, 483; 100/287; 269/221, 222, 223

[56] References Cited

U.S. PATENT DOCUMENTS

| | | | |
|---|---|---|---|
| 256,904 | 4/1882 | Laass | 100/287 |
| 293,401 | 2/1884 | Barrows | 100/287 |
| 2,629,312 | 2/1953 | Davis | 99/371 |
| 4,097,235 | 6/1978 | Stock | 99/371 |

FOREIGN PATENT DOCUMENTS

| | | |
|---|---|---|
| 27472 | 10/1972 | Australia . |
| 2481888 | 11/1981 | France . |
| 2594338 | 8/1987 | France . |
| 2605226 | 4/1988 | France . |

*Primary Examiner*—David A. Scherbel
*Assistant Examiner*—Reginald L. Alexander
*Attorney, Agent, or Firm*—Poms, Smith, Lande & Rose

[57] ABSTRACT

A holder for objects inside a rotating drum, particularly that of a sterilizer. The holder includes a pressure plate which can be brought into position for holding the objects by a motor-driven mechanism. This mechanism has a rod with threaded portions interacting with sleeves. These sleeves control the movement of pairs of link arms which are rigidly fixed to the pressure plate and are in contact with the drum wall.

25 Claims, 4 Drawing Sheets

HOLDER FOR OBJECTS INSIDE A ROTATING DRUM

The present invention has for an object a device for holding objects inside a rotating drum.

More precisely, the invention relates to a device for holding objects which are placed inside the rotating drum of apparatus such as sterilizers or the like.

Sterilization of objects or of products in the food or pharmaceutical industry such as tins, jars, receptacles, bottles, etc., is often effected in so-called autoclaves in which the products to be treated are introduced then removed after the treatment has terminated. These products to be treated are disposed in baskets, stackable trays or like elements. For certain of these products, the heat treatment for sterilization must be effected by a rotating movement of the product inside its packing. This movement of rotation is produced by the rotation, within the autoclave, of a drum containing baskets filled with the products to be sterilized. The same type of problem is raised for draining or tipping certain products on an apparatus other than an autoclave which is in that case called drainer or tipper. This operation allows elimination of the water deposited on these products by gravity during sterilization.

French Patent 86 02046 describes in detail an example of such a sterilization autoclave with rotating drum.

During rotation of the drum, it is necessary to avoid any movement of the products which might cause them damage or break them, by immobilizing them inside the drum with the aid of a holding device. In general, the individual products are stacked in troughs or placed on trays and it is the assembly of these troughs or trays which must be held inside the drum. To maintain the objects in place inside a rotating drum, it has already been proposed, as in French Patent Application FR-A-2 605 226, to control trays for holding the objects with the aid of jacks acting perpendicularly to the holding plate. Such a solution indeed makes it possible to obtain holding of the objects inside the drum, without manual intervention, but it is not satisfactory insofar as the effective holding of the objects depends on the correct functioning of the jacks and the supply system thereof. In addition, the functioning of jacks in an environment which may be aggressive or at least at high temperature, is unreliable.

It has also been proposed in U.S. Pat. No. 2,629,312 to ensure holding of objects inside a rotating drum with the aid of mechanisms for displacement of a pressure plate, this mechanism being actuated manually with the aid of a crank. This solution is hardly satisfactory insofar as the environment in which if must intervene is hostile and insofar as such manual interventions do not allow a chain for automatically treating the objects to be set up.

In order to overcome the drawbacks mentioned above, an object of the invention is to provide a device for maintaining objects in a rotating drum, particularly a sterilizer or like apparatus, which makes it possible, on the one hand, to ensure an efficient pressing of the product or the baskets containing the products in automatic manner and which, in addition, ensures such clamping in reliable manner during the whole operation of heat treatment corresponding, for example, to the sterilization of the products.

To attain this object, the device for holding objects in a rotating drum, according to the invention, is characterized in that it comprises at least one pressure plate presenting a substantially plane bearing face and means inside the drum for displacing the plate between a position of rest and a position of hold in which the bearing face of the plate is applied against the upper face of the objects to be held, the displacement means comprising:

- a rod mounted to rotate about its longitudinal axis and comprising n threaded portions, at least one portion having a direction of threading opposite that of the other threaded portion or portions;
- n tapped sleeves, each sleeve cooperating with one of the n threaded portions;
- n link arm systems, each system cooperating with one of the n sleeves and presenting one end articulated on said plate;
- a fluid motor coupled to the rod to provoke rotation thereof in two directions of rotation when the motor is supplied; and
- means for supplying the motor with fluid, the supply means traversing the end wall of the drum substantially along the axis of rotation thereof, whereby, in a first direction of rotation, the link arm systems bring said plate in its position of rest and, in a second direction of rotation, they bring said plate into position of hold.

It will be understood that pressing and holding of the objects in place is obtained by the displacement of the plate, itself obtained automatically by controlling the fluid motor. In addition, it will be understood that hold is ensured by the screw-nut (sleeve) and link arm system which is substantially self-locking in position of hold, which means that, even in the case of failure of the fluid motor, the objects remain efficiently held in place.

According to a first embodiment, each link arm system comprises a pair of assemblies forming link arms, each assembly of the same pair having a first end articulated on one of said sleeves and a second end articulated respectively on said plate and on a fixed element fast with said drum.

According to a second embodiment, the device is characterized in that it comprises a number 2p (2p=n) of link arm systems, grouped in two's, each link arm system comprising a pair of assemblies forming link arms, each assembly of the same pair having a first end articulated on one of said sleeves and a second end articulated respectively on the second ends of the assemblies forming link arms of the pair belonging to the same group, and one of said second ends being in addition articulated on said plate.

Other characteristics and advantages of the invention will appear more clearly upon reading the following description of several embodiments of the invention given by way of non-limiting example. The description refers to the accompanying Figures, in which.

Figure 1:
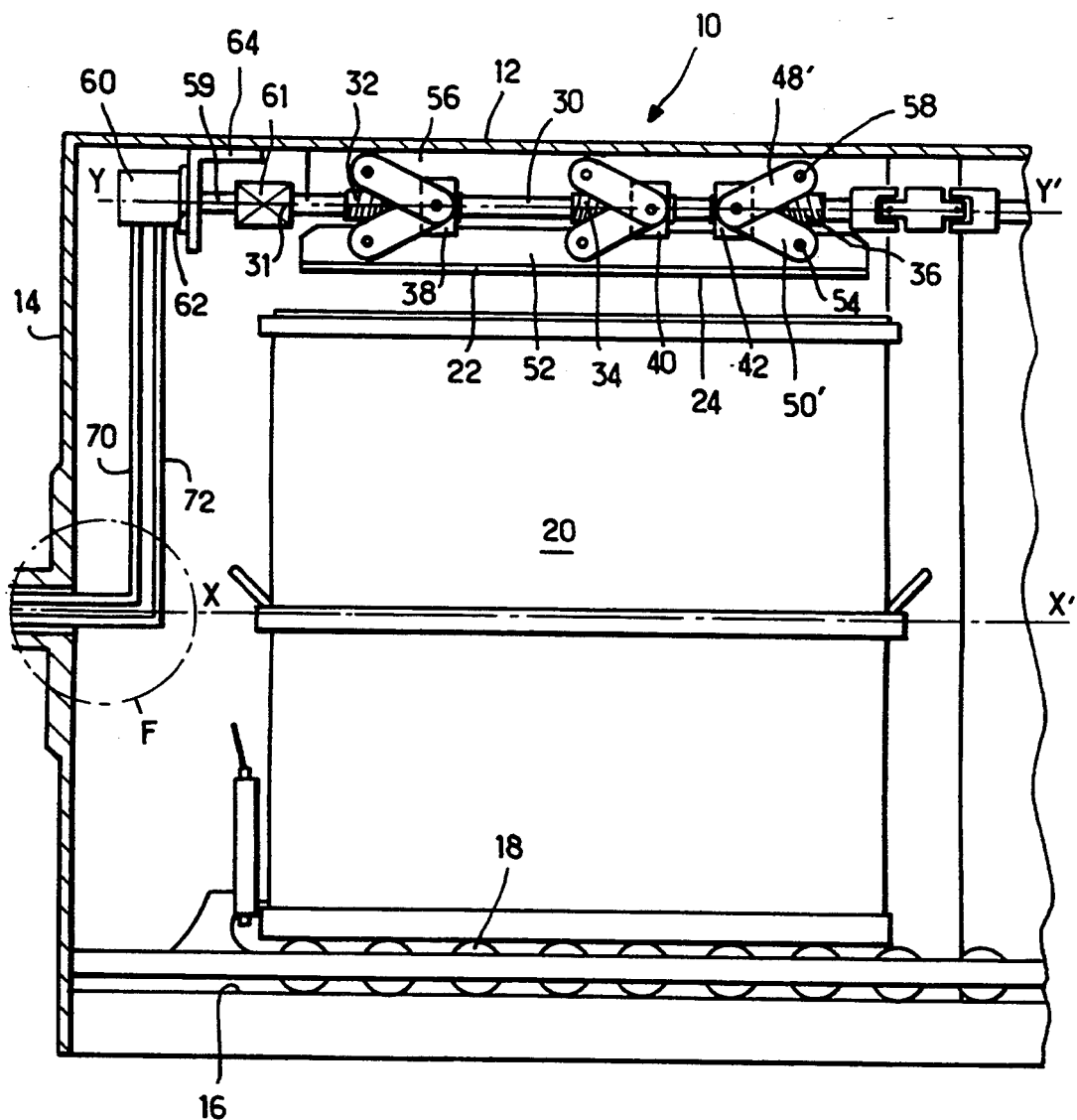
FIG. 1 is a view in vertical section of the rotating drum showing the holding mechanism in its position of rest.

Referring firstly to FIGS. 1 to 4, the assembly of the drum provided with its device for holding objects, according to a first embodiment, will be described. FIG. 1 shows the drum 10 constituted by a cylindrical lateral wall 12 whose axis XX' is at the same time the axis of rotation of drum 10, and by a circular end wall 14 whose periphery is welded to the lateral wall 12. In its lower part, the drum is provided with a floor 16 on which are mounted rollers 18 to facilitate introduction of the baskets 20 in which the objects to be sterilized are placed.

Figure 2:
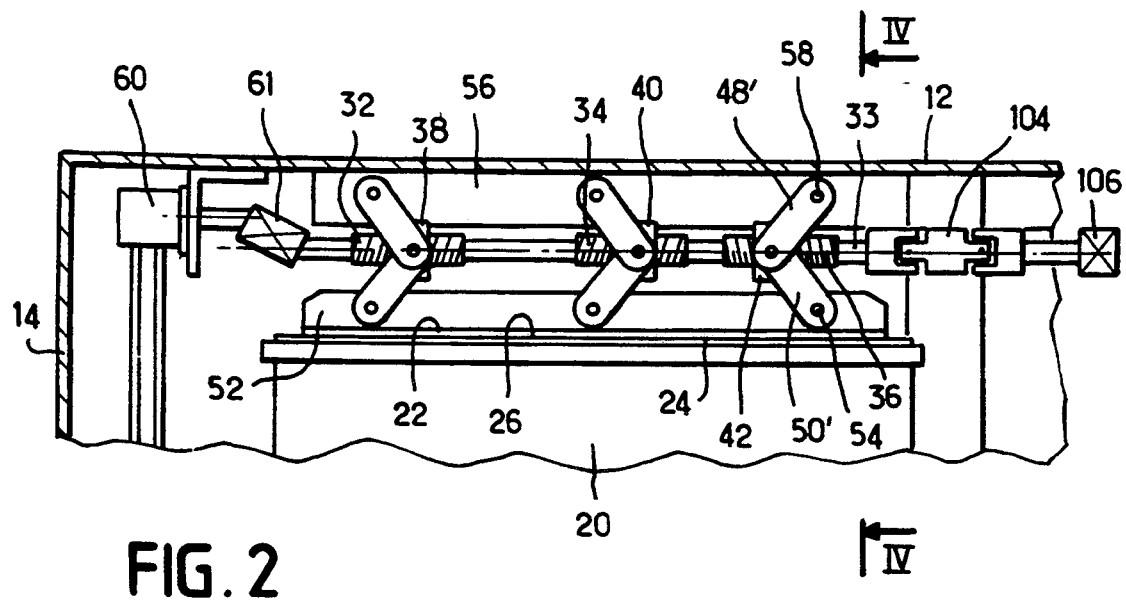
FIG. 2 is a partial view of the drum similar to that of FIG. 1 but showing the mechanical holding device in its work position.
Figure 4:
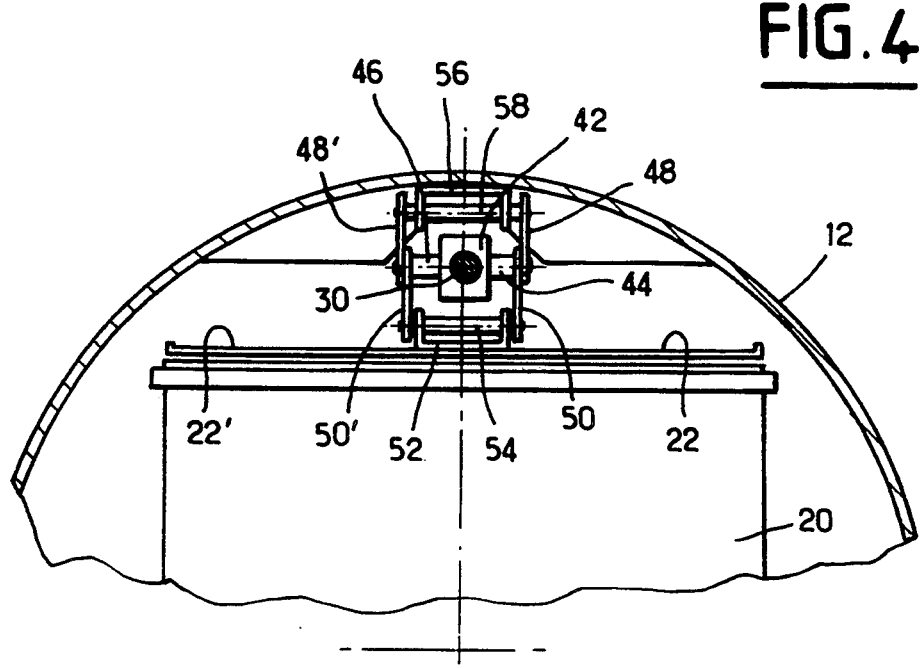
FIG. 4 is a partial view in section along line IV—IV of FIG. 2.

The holding device comprises a mobile plate 22 which may be displaced with the aid of a mechanism between a position of hold as shown in FIG. 2, in which the plate 22, or more precisely its lower face 24, is applied with pressure on the upper face 26 of the basket 20 and a position of rest shown in FIG. 1 in which the plate is moved away from the top 26 of the basket in order to allow introduction or removal thereof into or from the drum.

The displacement device is constituted by a rod 30 which may be set in rotation about its longitudinal axis YY', axis YY' being parallel to the axis of rotation XX' of drum 10. Rod 30 comprises a plurality of threaded portions. In the case of FIG. 1, the rod comprises three threaded portions referenced 32, 34 and 36 respectively. On each threaded portion is mounted a tapped sleeve, the tapped sleeves being respectively referenced 38, 40 and 42. On each side of the sleeves 38 to 42 are mounted half-shafts referenced 44 and 46 for the sleeve 42 shown in FIG. 4. These two half-shafts 44 and 46 are aligned. On each half-shaft 44, 46 is pivotally mounted a first end of two pairs of link arms respectively referenced 48, 48' and 50, 50' for the sleeve 42. As shown in the Figures, a U-angle 52 is fixed on the upper face 22' of the plate 22 and disposed in its longitudinal direction. Shafts such as 54 are engaged in orifices made in the sides of the angle 52. There are as many shafts as sleeves 38 to 42. In the same way, a U-angle 56 is fast with the top part of the lateral wall 12 of the drum. Shafts such as 58 are engaged in orifices made in the sides of the angle 56, the number of shafts 58 also being identical to the number of sleeves 38 to 42. The second ends of the upper link arms 48 and 50 are engaged at the ends of the upper shafts 58 and the second ends of the lower link arms 48' and 50' are engaged at the ends of shafts such as 54. It is seen that, in this way, three systems of link arms are reconstituted, which are, on the one hand, fast with the sleeves 38 to 42 and, on the other hand, respectively fast with the angle 56 connected to the drum and the angle 52 connected to the plate 22. The associated threads and tappings of the threaded parts 32 and 34 are in a first direction, the thread of the threaded part 36 being, of course, in a second direction.

It will thus be understood that, by rotating the rod 30 about its axis YY', the pairs of link arms will be spaced apart and the plate 22 lowered towards its position of hold and that, by rotating the rod in the opposite direction, the link arms are brought closer and the plate 22 is raised.

The end 31 of rod 30 is coupled to the shaft 59 of a pneumatic motor 60 of a type known per se, via a system 61 of the Universal joint type. Motor 60 is provided with a flange 62 which is fixed on a bracket 64 fast with the top part of the lateral wall 12 of the drum.

It will be understood that, thanks to the presence of the Universal joint system 61, motor 60 transmits the torque to rod 30 in all the positions that the latter occupies during its rotation under the effect of the link arms 48, 48'.

Instead of using a pneumatic motor, it would be possible to employ a hydraulic motor, on condition that a control liquid is chosen which is adapted to the temperature conditions prevailing inside the drum.

Motor 60 is supplied via two conduits 70 and 72 to allow the two directions of rotation of the motor. The two conduits 70 and 72 are supplied with compressed air via two rotating joints which are more readily visible in FIG. 5, which will be described hereinafter.

Figure 5:
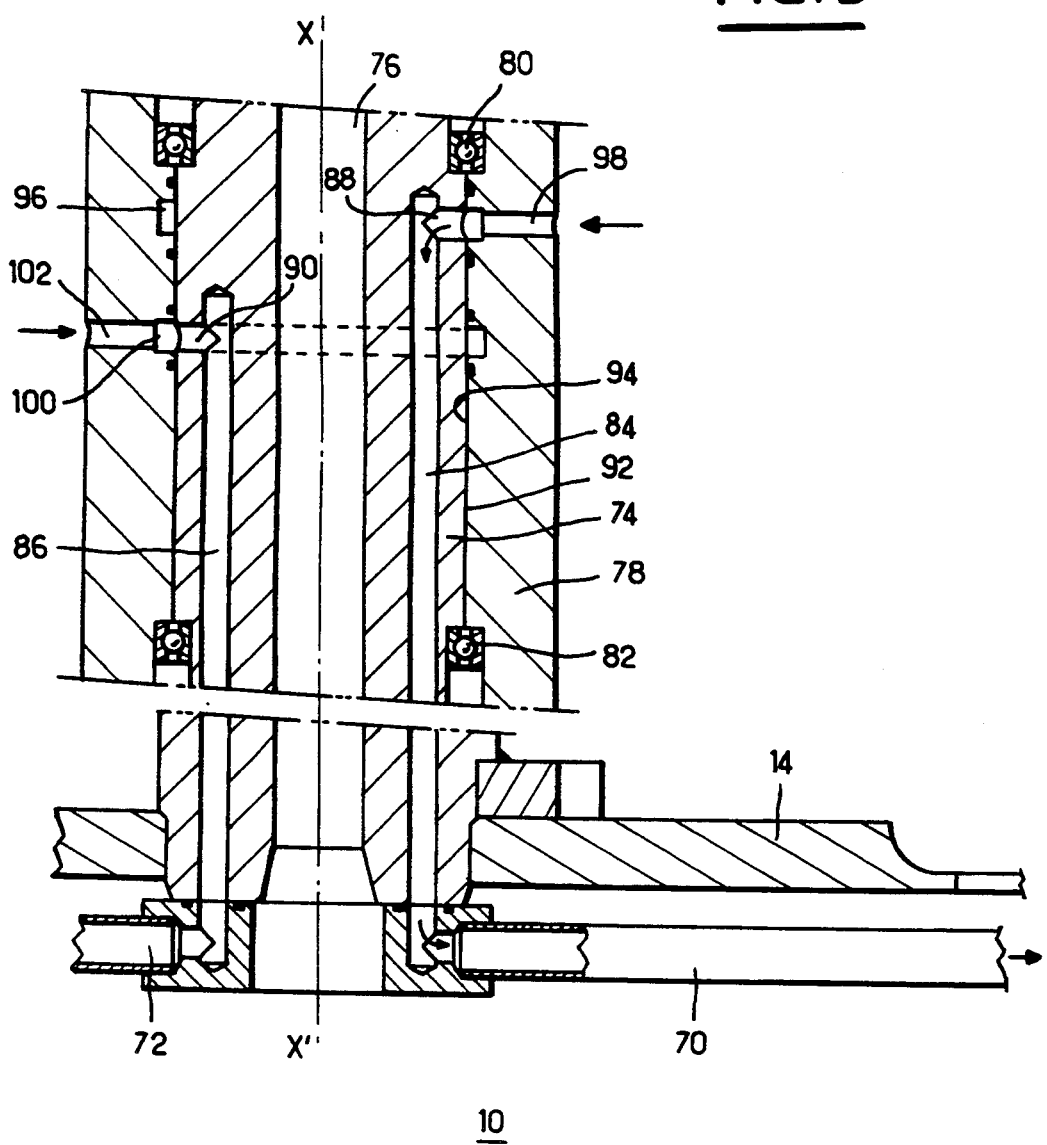
FIG. 5 is a view in detail of part F of FIG. 1, detailed view which shows the passage of the supply conduits of the fluid motor towards the wall of the drum.

The end wall 14 of the drum 10 is fast with a shaft 74 for rotation disposed along axis XX' of the drum. Shaft 74 comprises an axial channel 76 for the possible introduction of probes in the drum. Shaft 74 is mounted to rotate in a fixed bearing 78 via roller bearings 80 and 82. Shaft 74 is in addition pierced with two blind conduits 84 and 86. The blind end of each conduit is connected to radial pipes respectively referenced 88 and 90. The pipes 88 and 90 open out in the outer wall 92 of the shaft 74. Opposite the pipe 88, the inner wall 94 of the bearing 78 is provided with a circular groove 96 itself connected to a radial supply pipe 98 made in the fixed bearing 78. Symmetrically, opposite pipe 90, the inner wall 94 of the bearing 78 is provided with a circular groove 100 connected to a second supply pipe 102. 0-rings 104, 106, 108, 110 are mounted on either side of the annular grooves 96 and 100. As shown in FIG. 5, the open end of the pipes 84 and 86 is connected to the ends of pipes 70 and 72. In this way, by this double rotary joint system, the motor 60 may be permanently supplied either with the compressed air applied to the fixed pipe 102, or with the compressed air applied to fixed pipe 98.

If reference is again made to FIGS. 1 and 2, it is seen that the second end 33 of the rod 30 may be connected, via a Universal joint system 104, to a manual rotation-imparting member 106 constituted for example by a crank. In this case, even in the event of failure of the motor 60, it is possible to control rotation of the rod and therefore the movements of the plate 22, manually.

Figure 3:
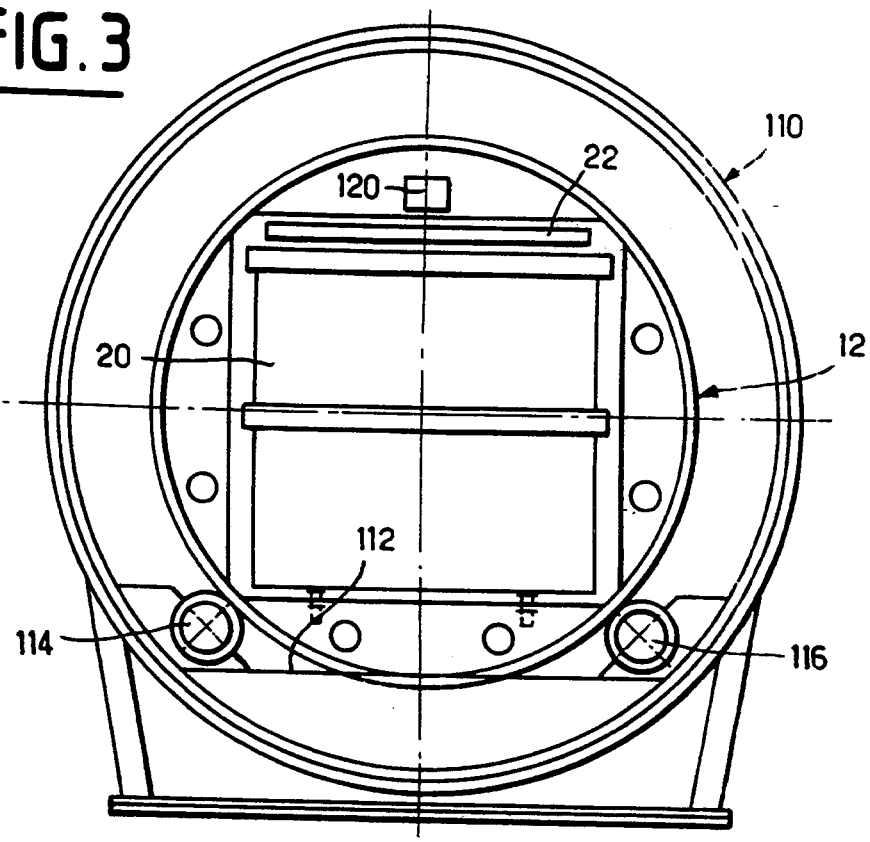
FIG. 3 is a view from the right of the drum of FIG. 1 mounted in the enclosure of a sterilization autoclave.

FIG. 3 shows the drum 10 mounted in the autoclave enclosure of a sterilizer. This FIG. shows the outer envelope 110 of the sterilization with its "floor" 112 on which are mounted two support rollers 114 and 116 mounted idly to guide the lateral wall 12 of the drum 10 during its rotation. FIG. 3 also shows the baskets 20 containing the products to be sterilized, the presser plate 22 and, in symbolic form, the device 120 for displacement of the plate 22.

Figure 6:
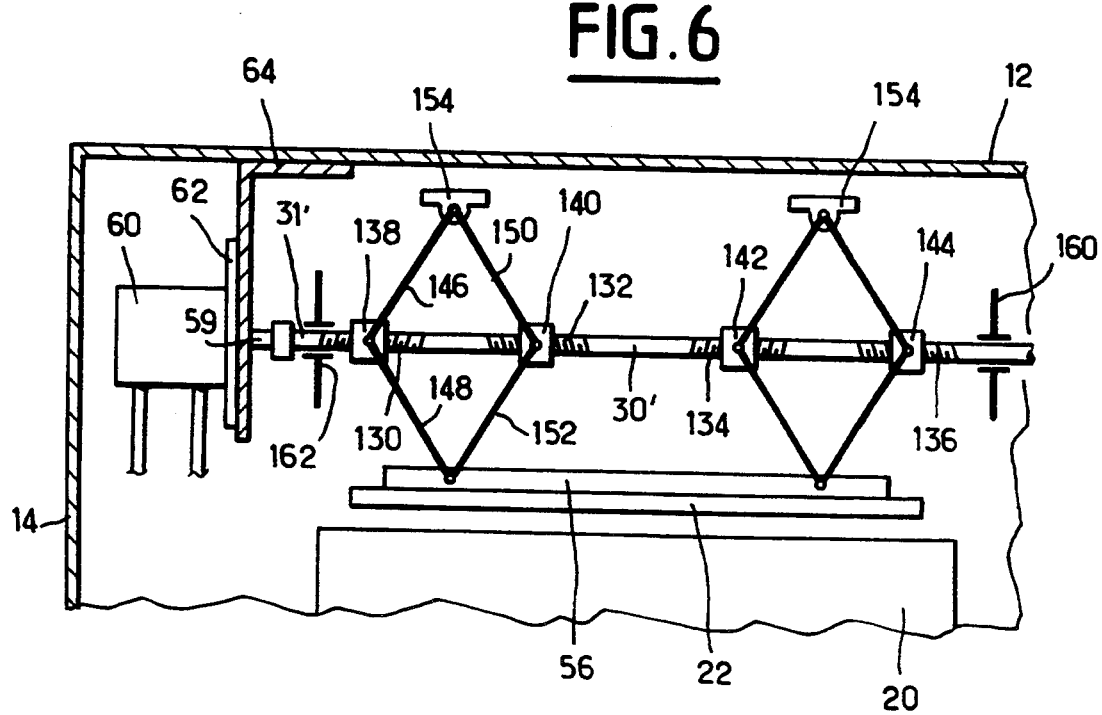
FIG. 6 is a simplified view of a second embodiment of the plate displacement means.

FIG. 6 shows, in simplified form, a second embodiment of the means for displacing the plate 22. The rod 30' comprises four threaded portions 130, 132, 134 and 136 with alternately reversed pitches. On the threaded portions are mounted four sleeves 138, 140, 142 and 144. On each sleeve are articulated the first ends of two link arms, 146 and 148 for sleeve 138 and 150 and 152 for sleeve 140. The second ends of the link arms 148 and 150 are articulated on each other and on the "shoe" 154. Symmetrically, the second ends of the link arms 148 and 152 are articulated on each other and on the angle 56 fast with the plate 22. The link arms 156 to 162 associated with the sleeves 142 and 144 are mounted in the same way. Two deformable parallelograms are thus constituted whose configuration is controlled by the relative position of the groups of sleeves 130, 132 and 134, 136.

The end 31' of the rod 30' is directly fast with the end of the shaft 59 of the pneumatic motor 60. The latter is fixed on the bracket 64 via the flange 62. It will be understood that, by controlling the motor 60 in a first direction, the apices of the parallelograms bearing the shoes 154 and the plate 22 move apart mutually until the shoes 154 come into contact with the top part of the lateral wall 12 of the drum, and that, simultaneously, the plate 22 is applied against the upper face of the baskets 20. The baskets are then held perfectly. By controlling the rotation of the motor 60 in the other direction, the shoes 154 and the plate 22 are moved closer towards the rod 30', which releases the baskets 20.

It will be understood that this second embodiment presents the same advantages as the first embodiment. An additional advantage resides in the fact that the rod 30' is immobilized in translation, which makes it possible to mount its ends in two bearings 160 and 162 fast with the drum 10. On the other hand, it is necessary to effect a very precise positioning of the rod 30' for the shoes 154 to come into abutment against the wall 12 at the same time as plate 22 comes into contact with the upper face of the baskets 20. This implies that this second embodiment is very well adapted to the case of the objects loaded in the rotary drum always presenting the same height. On the contrary, in the case of the first embodiment, the holding device is adapted to different heights of objects.

In the foregoing description, only the case of the holding device comprising one sole pressure plate has been considered. It goes without saying that the invention would not be exceeded if the rod 30 or 30' served to control several separate pressure plates, via link arm systems.

We claim:

1. A device for holding objects inside a rotating drum, the objects having a first face resting on a support fixed relative to the drum and a second face which is substantially planar and the drum having a rotation axis, said device comprising:
   a pressure plate having a substantially planar bearing face; and
   displacement means inside the drum for displacing said plate between a rest position and a hold position wherein said bearing face is applied against the second face of the objects;
   wherein said displacement means comprises:
   (a) a rod mounted to rotate about a longitudinal axis thereof parallel to the drum rotation axis, said rod including a plurality of threaded portions, at least one threaded portion having a direction of threading opposite that of another said threaded portion;
   (b) a plurality of tapped sleeves, each cooperating with one of said threaded portions;
   (c) a plurality of link arm systems, each cooperating with one said sleeve and each having one end thereof articulated on said plate, wherein the number of said plurality of systems is equal to the number of said plurality of threaded portions;
   (d) a fluid motor coupled to said rod to provoke rotation thereof in alternative first and second directions of rotation when said motor is supplied with fluid pressure; and
   (e) supply means for supplying said motor with fluid under pressure, said supply means traversing a wall of the drum substantially along the drum rotation axis, such that in a first direction of rotation, said systems bring said plate to the rest position and in a second direction of rotation, said systems bring said plate to the hold position.

2. A device according to claim 1, wherein each said system comprises a pair of assemblies forming link arms, each assembly of the same pair having a first end articulated on one of said sleeves and a second end articulated respectively on said plate and on an element fixed relative to the drum.

3. A device according to claim 2, wherein an end of said rod not connected to said motor is connectable to a member for manually routing said rod.

4. A device according to claim 2, wherein said supply means includes a pair of pipes arranged in a shaft for routing the drum, each of said pipes being operatively connected to a rotary joint system, and at least two conduits positioned inside the drum and connected to said pipes.

5. A device according to claim 2, wherein said motor is a pneumatic motor.

6. A device according to claim 2, wherein said rod is free in translation in a direction of displacement of said plate, said motor is fixed relative to the drum and said motor has a shaft which is connected to one end of said rod by a mechanical system adapted to transmit rotational movement while allowing relative translational movement between said shaft and said rod.

7. A device according to claim 6, wherein an end of said rod not connected to said motor is connectable to a member for manually rotating said rod.

8. A device according to claim 6, wherein said supply means includes a pair of pipes arranged in a shaft for routing the drum, each of said pipes being operatively connected to a rotary joint system, and at least two conduits positioned inside the drum and connected to said pipes.

9. A device according to claim 6, wherein said motor is a pneumatic motor.

10. A device according to claim 1, wherein each said link arm system comprises a pair of link arm systems, each one of said pair comprising a pair of assemblies forming link arms, each assembly of the same pair of assemblies having a first end articulated on one of said sleeves and a second end articulated respectively on second ends of said assemblies forming link arms of the pair belonging to the same group, and one of said second ends being articulated on said plate.

11. A device according to claim 10, wherein an end of said rod not connected to said motor is connectable to a member for manually rotating said rod.

12. A device according to claim 10, wherein said supply means includes a pair of pipes arranged in a shaft for rotating the drum, each of said pipes being operatively connected to a rotary joint system, and at least two conduits positioned inside the drum and connected to said pipes.

13. A device according to claim 10, wherein said motor is a pneumatic motor.

14. A device according to claim 10, wherein said rod is immobile in translation, said motor is fixed relative to the drum and said motor includes a shaft which is directly connected to one end of said rod.

15. A device according to claim 14, wherein an end of said rod not connected to said motor is connectable to a member for manually rotating said rod.

16. A device according to claim 14, wherein said supply means includes a pair of pipes arranged in a shaft for rotating the drum, each of said pipes being operatively connected to a rotary joint system, and at least two conduits positioned inside the drum and connected to said pipes.

17. A device according to claim 14, wherein said motor is a pneumatic motor.

18. A device according to claim 1, wherein an end of said rod not connected to said motor is connectable to a member for manually rotating said rod.

19. A device according to claim 18, wherein said supply means includes a pair of pipes arranged in a shaft for rotating the drum, each of said pipes being operatively connected to a rotary joint system, and at least two conduits positioned inside the drum and connected to said pipes.

20. A device according to claim 18, wherein said motor is a pneumatic motor.

21. A device according to claim 1, wherein said supply means includes a pair of pipes arranged in a shaft for rotating the drum, each of said pipes being operatively connected to a rotary joint system, and at least two conduits positioned inside the drum and connected to said pipes.

22. A device according to claim 21, wherein said motor is a pneumatic motor.

23. A device according to claim 1, wherein said motor is a pneumatic motor.

24. A device according to claim 1, wherein said number is three.

25. A device according to claim 1, wherein said number is four.

* * * * *